US010612097B2

(12) United States Patent
List

(10) Patent No.: US 10,612,097 B2
(45) **Date of Patent: *Apr. 7, 2020**

(54) RNF41 AS A BIOMARKER PREDICTING RESPONSE TO LENALIDOMIDE IN NON-DEL(5Q) MDS

(71) Applicant: H. LEE MOFFITT CANCER CENTER AND RESEARCH INSTITUTE, INC., Tampa, FL (US)

(72) Inventor: Alan List, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/682,062

(22) Filed: Aug. 21, 2017

(65) Prior Publication Data

US 2018/0073078 A1 Mar. 15, 2018

Related U.S. Application Data

(63) Continuation of application No. 14/648,306, filed as application No. PCT/US2013/073284 on Dec. 5, 2013, now Pat. No. 9,738,933.

(60) Provisional application No. 61/733,703, filed on Dec. 5, 2012.

(51) Int. Cl.

| | |
|---|---|
| ***C12Q 1/68*** | (2018.01) |
| ***G01N 33/574*** | (2006.01) |
| ***C12Q 1/6883*** | (2018.01) |
| ***G01N 33/573*** | (2006.01) |
| ***A61K 45/06*** | (2006.01) |
| ***A61K 31/454*** | (2006.01) |

(52) U.S. Cl.

CPC .......... *C12Q 1/6883* (2013.01); *A61K 31/454* (2013.01); *A61K 45/06* (2013.01); *G01N 33/573* (2013.01); *G01N 33/57426* (2013.01); *C12Q 2600/106* (2013.01); *C12Q 2600/158* (2013.01); *G01N 2333/9015* (2013.01); *G01N 2800/52* (2013.01)

(58) Field of Classification Search

None

See application file for complete search history.

(56) References Cited

FOREIGN PATENT DOCUMENTS

| | | |
|---|---|---|
| WO | 2010006291 A1 | 1/2010 |
| WO | 2012083274 A2 | 6/2012 |

OTHER PUBLICATIONS

Ebert et al (PLoS Medicine, 2008, 5:312-322).*
Scott et al (Annual Review of Medicine, 2010, 61:345-358).*
GeneAnnot website, probesets for RNF41 (printed Mar. 2019).*
List et al., Efficacy of lenalidomide in myelodysplastic syndromes, N. Eng. J. Med. 352:549 (2005).
Ebert et al., An Erythroid Differentiation Signature Predicts Response to Lenalidomide in Myelodysplastic Syndrome, PLoS Medicine 5(2):e35(2008).
International Preliminary Report on Patentability for International Application No. PCT/US2013/073284 dated Jun. 9, 2015.
Ito et al., Identification of a primary target of thalidomide teratogenicity, Science 327:1345-50 (2010).
Zhu, et al., Cereblon expression is required for the antimyeloma activity of lenalidomide and pomalidomide, Blood 118:4771-4779 (2011).
International Search Report and Written Opinion for International Application No. PCT/US2013/073284 dated Mar. 11, 2014.
Basiorka et al., Lenalidomide upregulates erythropoietin receptor expression through inhibition of the E3-Ubiquitin Ligase Ring Finger Protein 41 (RNF41), 54th American Society of Hematology Annual Meeting and Exposition.
Sugimoto, et al., Cytogenetic and molecular predictors of response in patients with myeloid malignancies without del [5q] treated with lenalidomide, Journal of Hematology & Oncology, vol. 5, Article No. 4, pp. 1-10, 2012.
Giagounidis, Lenalidomide for del (5q) and non-del myelodysplastic syndromes, Seminars in Hematology, vol. 49, No. 4, pp. 312-322 2012.
Chen et al. (Cancer Research, 2010, 70:5994-6003).
GeneAnnot website, probesets for RNF41 (printed Nov. 2016).
Pellagatti et al. (PNAS, 2007, 104:11406-11411).
GeneAnnot website, probesets for RNF41, printed May 2016.

* cited by examiner

*Primary Examiner* — Laura B Goddard
(74) *Attorney, Agent, or Firm* — Meunier Carlin & Curfman LLC

(57) ABSTRACT

Disclosed herein is a method of using erythroid expression levels of RNF41 as a predictive biomarker for responsiveness to lenalidomide (LEN) in patients with non-del(5q) MDS.

8 Claims, 3 Drawing Sheets

RNF41 AS A BIOMARKER PREDICTING RESPONSE TO LENALIDOMIDE IN NON-DEL(5Q) MDS

CROSS-REFERENCE TO RELATED APPLICATIONS

This application claims benefit of U.S. Provisional Application No. 61/733,703, filed Dec. 5, 2013, which is hereby incorporated herein by reference in its entirety.

TECHNICAL FIELD

This application relates generally to biomarkers for predicting response to lenalidomide in non-del(5q) meylodysplastic syndrome (MDS).

BACKGROUND

Lenalidomide (LEN) and its analogue, pomalidomide, promote erythroid lineage competence and in vitro colony-forming capacity. The best results with LEN are obtained in patients with deletion 5q. In patients with non-del(5q) MDS, LEN restores erythropoiesis in only a subset of patients (List, et al. N. Eng. J. Med. 352:549 (2005)). Such responders to LEN treatment display repression of erythroid-specific genes and that LEN restored transcriptional response to erythropoietin (Epo) (Ebert, et al. PLoS Medicine 5(2):e35 (2008)). This could suggest that LEN enhances Epo receptor (R) signal fidelity. LEN induces cellular expression of JAK2-associated EpoR in a concentration-dependent manner (Basiorka, et al. Blood. 118: 2382a (2011)). However, the mechanism of this regulation was unclear.

The cereblon RING (really interesting new gene) finger domain containing E3-ubiquitin ligase complex has been implicated as a key target of the immunomodulatory drugs (IMiDs) responsible for the teratogenic effects of thalidomide and the cytotoxic effects of LEN in multiple myeloma (Ito et al. Science. 327:1345-50 (2010); Zhu, et al. Blood. 118:4771-4779 (2011)). LEN interacts with the RING finger E3 ubiquitin ligase, murine double minute 2 (MDM2) to inhibit ligase ubiquitination, and stabilize the protein (Wei et al. Oncogene, MS#ONC-2011-01840R (2012)).

However, biomarkers are still needed that predict responsiveness to LEN in subjects with non-del(5q) MDS. Moreover, additional therapeutics are needed to treat subjects with non-del(5q) MDS, especially those that are not responders to LEN treatment.

SUMMARY

Disclosed herein is a method of using erythroid expression levels of RNF41 as a biomarker for response to lenalidomide (LEN) in patients with non-del(5q) MDS. Approximately 70% of newly diagnosed MDS patients have a non-del(5q). While MDS patients with a del(5q) are already approved to receive lenalidomide, MDS patients with a non-del(5q) are not. That is partially because only 26% of these patients are likely to be responsive to treatment. As disclosed herein, the RNF41 biomarker can be used to determine which patients are among the approximately 26% of non-del(5q) patients that are likely to respond to lenalidomide, and which patients are among the 74% that are likely not to respond.

DESCRIPTION OF DRAWINGS

FIG. 2 includes pre and post-treatment images for a responder and a non-responder. The intensity of RNF41 in the erythroid stained cells in included below each image.

DETAILED DESCRIPTION

Figure 1:
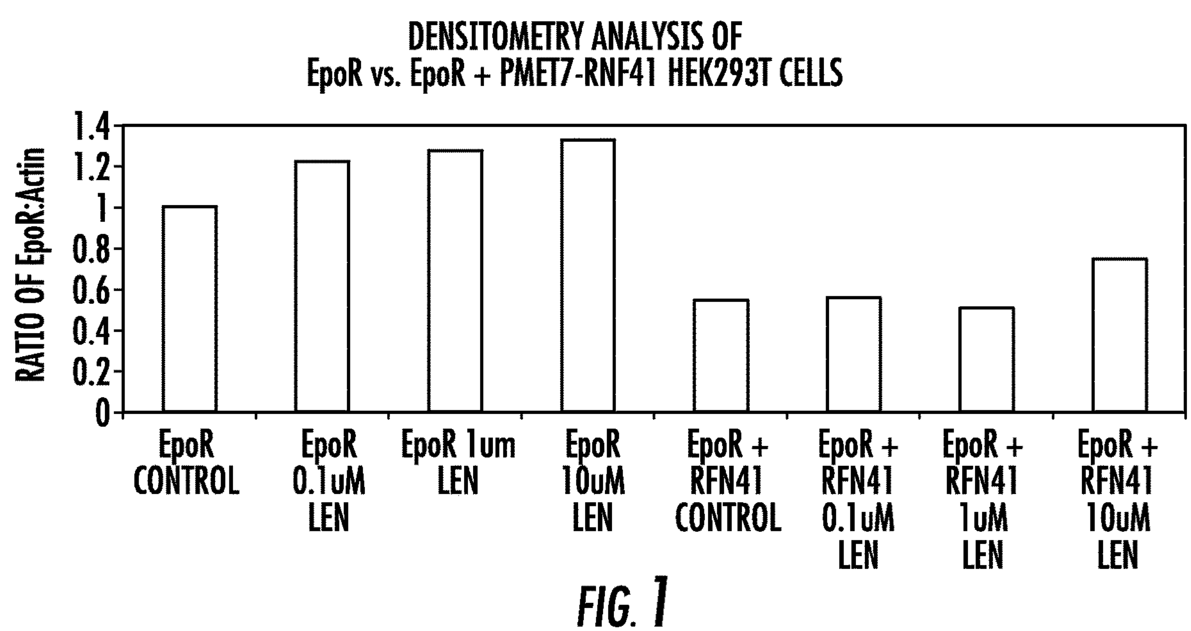
FIG. 1 is a bar graph plotting the ratio of EpoR/Actin in EpoR and EpoR+pMet7-RNF41 HEK293T cells treated with increasing concentrations of LEN (0 μM (control), 0.1 μM, 1 μM, and 10 μM).

Ring Finger Protein 41 (RNF41) is shown herein to inhibit efficacy of lenalidomide (LEN) to promote erythroid competence in a subject with non-del(5q) meylodysplastic syndrome (MDS). Moreover, the relative baseline expression of RNF41 in erythroid cells is shown herein to be greater in non-responders than in responders to LEN treatment.

Therefore, a method of predicting therapeutically effective response of a subject with non-del(5q) MDS to LEN, or a functional derivative thereof, is disclosed. The method involves measuring erythroid expression levels of RNF41 in a sample from the subject prior to treatment with LEN. In responders, LEN treatment restores transcriptional response to erythropoietin (Epo) and enhances EpoR signal fidelity.

Therefore, if the levels of RNF41 in the subject's sample are within control values for responders, or are reduced compared to a non-responder control value, the method can further involve administering to the subject a therapeutically effective dose of LEN. For example, the method can further involve administering to the subject a therapeutically effective dose of LEN if the mean levels of RNF41 are reduced compared to a value from a control sample from a known non-responder by at least 5%, 10%, 15%, or 20%. The method can further involve administering to the subject a therapeutically effective dose of LEN if the mean levels of RNF41 are within 5%, 10%, 15%, or 20% of the mean control value for responders.

The method identifies those subjects that are not expected to be responsive to LEN treatment. Therefore, in some embodiments, the method involves ceasing treatment in those subjects having RNF41 levels within control values for non-responders, or RNF41 levels that are elevated compared to responder control values. For example, the method can further involve ceasing treatment if the mean levels of RNF41 are elevated compared to a value from a control sample from a known responder by at least 5%, 10%, 15%, or 20%. The method can further involve ceasing treatment if the mean levels of RNF41 are within 5%, 10%, 15%, or 20% of the mean control value for non-responders.

If the mean levels of RNF41 are elevated compared to a value from a control sample from a known responder, then the method can involve selecting an alternative therapy for the subject. For example, the method can comprise selecting an alternative therapy to administer with or instead of LEN if the mean levels of RNF41 are elevated by at least 5%, 10%, 15%, or 20% compared to a value from a control sample from a known responder. In some embodiments, the method comprises treating the subject with 5-azacitidine or decitabine if the mean levels of RNF41 are elevated by at least 10% compared to a value from a control sample from a known responder. In some embodiments, the method comprises treating the subject with recombinant erythropoietins or antithymocyte globulin if the mean levels of RNF41 are elevated by at least 10% compared to a value from a control sample from a known responder.

Other suitable chemotherapeutic drugs suitable for treating non-responsive patients can be used. The majority of chemotherapeutic drugs can be divided in to: alkylating agents, antimetabolites, anthracyclines, plant alkaloids, topoisomerase inhibitors, monoclonal antibodies, and other antitumour agents. All of these drugs affect cell division or DNA synthesis. Some newer agents don't directly interfere with DNA. These include the new tyrosine kinase inhibitor imatinib mesylate (Gleevec® or Glivec®), which directly targets a molecular abnormality in certain types of cancer (chronic myelogenous leukemia, gastrointestinal stromal tumors). In addition, some drugs can be used which modulate tumor cell behavior without directly attacking those cells. Hormone treatments fall into this category of adjuvant therapies.

The method can involve measuring RNF41 protein expression levels in the sample. Various immunodetections methods are available for detecting RNF41 protein expression. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such RNF41) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as RNF41) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

The method can also involve measuring RNF41 mRNA expression levels in the sample. A number of widely used procedures exist for detecting and determining the abundance of a particular mRNA in a total or poly(A) RNA sample. For example, specific mRNAs can be detected using Northern blot analysis, nuclease protection assays (NPA), in situ hybridization, or reverse transcription-polymerase chain reaction (RT-PCR).

Also disclosed is a method of treating a subject with non-del(5q) MDS that involves administering to the subject an RNF41 inhibitor in an amount effective to reduce the inhibitory effect of RNF41 on LEN-induced EpoR upregulation. Suitable RNF41 inhibitors include any agent capable of inhibiting one or more activities of RNF41. "Activities" of a protein include, for example, transcription, translation, intracellular translocation, secretion, phosphorylation by kinases, cleavage by proteases, homophilic and heterophilic binding to other proteins, ubiquitination. Therefore, in some embodiments, the RNF41 inhibitor is a molecule, such as an antibody, that selectively binds RNF41 and prevents it from binding, for example, EpoR. In other embodiments, the RNF41 inhibitor is a functional nucleic acid that inhibits RNF41 gene expression.

In some embodiments, the RNF41 inhibitor is a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. Functional nucleic acid molecules can interact with any macromolecule, such as DNA, RNA, polypeptides, or carbohydrate chains. Thus, functional nucleic acids can interact with the mRNA of RNF41 or the genomic DNA of RNF41 or they can interact with the RNF41 polypeptide. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a polypeptide for example, that the background molecule be a different polypeptide.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $K_d$ less than 10−6, 10−8, 10−10, or 10−12.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells.

Gene expression can also be effectively silenced in a highly specific manner through RNA interference (RNAi). This silencing was originally observed with the addition of double stranded RNA (dsRNA). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends. In an ATP dependent step, the siRNAs become integrated into a multi-subunit protein complex, commonly known as the RNAi induced silencing complex (RISC), which guides the siRNAs to the target RNA sequence. At some point the siRNA duplex unwinds, and it appears that the antisense strand remains bound to RISC and directs degradation of the complementary mRNA sequence by a combination of endo and exonucleases. However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. Disclosed herein are any siRNA designed as described above based on the sequences for RNF41. The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

Also provided is a method of identifying an agent that can be used to treat non-del(5q) MDS. The method can comprise providing a sample comprising RNF41 under conditions that allow the binding of RNF41 and EpoR, contacting the sample with a candidate agent, detecting the level of RNF41/EpoR binding, comparing the binding level to a control, a decrease in RNF41/EpoR binding compared to the control identifying an agent that can be used to treat an inflammatory disease.

The binding of RNF41 to EpoR can be detected using routine methods, such as immunodetection methods, that do not disturb protein binding. The methods can be cell-based or cell-free assays. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

The binding of RNF41 to EpoR can be detected using fluorescence activated cell sorting (FACS). For example, disclosed are cell lines transfected with RNF41 and EpoR optionally fused to fluorescent proteins. These cell lines can facilitate high-throughput screens for biologically expressed and small molecule binding to RNF41 and EpoR in their physiological forms.

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) used.

Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from purveyors of chemical libraries including but not limited to ChemBridge Corporation (16981 Via Tazon, Suite G, San Diego, Calif., 92127, USA, www.chembridge.com); ChemDiv (6605 Nancy Ridge Drive, San Diego, Calif. 92121, USA); Life Chemicals (1103 Orange Center Road, Orange, Conn. 06477); Maybridge (Trevillett, Tintagel, Cornwall PL34 0HW, UK)

Alternatively, libraries of natural compounds in the form of bacterial, fungal, plant, and animal extracts are commercially available from a number of sources, including O2H, (Cambridge, UK), MerLion Pharmaceuticals Pte Ltd (Singapore Science Park II, Singapore 117528) and Galapagos NV (Generaal De Wittelaan L11 A3, B-2800 Mechelen, Belgium).

In addition, natural and synthetically produced libraries are produced, if desired, according to methods known in the art, e.g., by standard extraction and fractionation methods or by standard synthetic methods in combination with solid phase organic synthesis, micro-wave synthesis and other rapid throughput methods known in the art to be amenable to making large numbers of compounds for screening purposes. Furthermore, if desired, any library or compound, including sample format and dissolution is readily modified and adjusted using standard chemical, physical, or biochemical methods.

Candidate agents encompass numerous chemical classes, but are most often organic molecules, e.g., small organic compounds having a molecular weight of more than 100 and less than about 2,500 Daltons. Candidate agents can include functional groups necessary for structural interaction with proteins, particularly hydrogen bonding, and typically include at least an amine, carbonyl, hydroxyl or carboxyl group, for example, at least two of the functional chemical groups. The candidate agents often contain cyclical carbon or heterocyclic structures and/or aromatic or polyaromatic structures substituted with one or more of the above functional groups.

In some embodiments, the candidate agents are proteins. In some aspects, the candidate agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and vertebrate proteins, and human proteins.

The disclosed compositions can be used therapeutically in combination with a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art, including solutions such as sterile water, saline, and buffered solutions at physiological pH. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally, transdermally, extracorporeally, ophthalmically, intranasally, or by inhalation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The disclosed compositions may be administered prophylactically to patients or subjects who are at risk for MDS or multiple myeloma. Thus, the method can further comprise identifying a subject at risk for MDS or multiple myeloma prior to administration of the disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, a typical daily dosage of the disclosed agents used alone might range from about 1 μg/kg to up to 100 mg/kg of body weight or more per day, depending on the factors mentioned above. In some embodiments, lenalidomide is administered at a dose of about 5-10 mg/day. In these or other embodiments, dexamethasone can be administered orally to the subject at a dose of about 10 to 30 mg weekly, including about 20 mg weekly.

Also disclosed is a kit for treating a subject with non-del (5q) meylodysplastic syndrome (MDS). The kit can contain lenalidomide (LEN) and an assay for detecting expression levels of Ring Finger Protein 41 (RNF41). For example, the assay can be an immunoassay comprising an antibody that specifically binds RNF41. In these embodiments, the assay can further comprises secondary antibodies and reagents for detecting binding of the RNF41-specific antibody to RNF41. Examples of suitable immunoassays include enzyme-linked immunosorbent assay (ELISA), immunohistochemistry, and flow cytometery. In other embodiments, the assay contains one or more oligonucleotides that function as primers or probes for detecting RNF41 gene expression levels. For example, the oligonucleotide can be conjugated to a detection label. The assay can also further contain polymerase chain reaction (PCR) enzymes and buffers. In any case, the assay can further contain RNF41 protein or cDNA to serve as a control. In addition, the kit assay can further contain reference values of RNF41 for responders and/or non-responders. Further, the kit can contain instructions that identify an RNF41 expression range for effective LEN treatment based on values from responders and/or non-responders.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "sample from a subject" refers to any bodily sample containing erythrocytes, such as a blood or a bone marrow sample.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

EXAMPLES

Example 1: Lenalidomide (LEN) Upregulates Erythropoietin Receptor Expression Through Inhibition of the E3-Ubiquitin Ligase Ring Finger Protein 41 (RNF41)

The effect of LEN on the E3-ubiquitin ligase, RNF41, which regulates steady state or ligand independent, Janus kinase (JAK2)-associated Type I receptor internalization, was investigated.

Lenalidomide (LEN) Treatment Stabilizes Cellular Erythropoietin Protein Receptor (EpoR)

UT-7 cells (a cell line established from the bone marrow of a patient with acute megakaryoblastic leukemia) were treated with cycloheximide (CHX)±1 μM LEN for 0, 32, 40, 48, 56, 64, and 72 hours. The samples were then separated by SDS-PAGE, and immunoblotted with EpoR antibodies.

Treatment of the UT-7 erythroid progenitor cell line with cycloheximide+1 uM LEN showed that LEN stabilized cellular EpoR (T1/2, LEN>72 h vs. 56 h) compared to treatment with CHX alone.

Effects of Lenalidomide on Receptor Turnover are Restricted to Type 1 Cytokine Receptors To examine if the effects of LEN on receptor turnover are restricted to Type 1 cytokine receptors, the effects of LEN on cellular expression of IL3-R (Type 1) and c-Kit (Type 2) were examined. UT-7 cells were treated with increasing concentrations of LEN (0 μM (control), 0.1 μM, 1 μM, and 10 μM) for 1 hour. Samples were separated by SDS-PAGE and immunoblotted with IL3-R (Type 1) and c-Kit (Type 2) antibodies. Upregulation of IL3-R occurred in a concentration-dependent manner, whereas expression of c-Kit remained unchanged. This suggested Type 1 receptor specificity.

Treatment with Lenalidomide Upregulates RNF41 Binding to EpoR

To determine if LEN alters EpoR/RNF41 interaction, protein association after LEN treatment was examined. UT-7 cells were treated with increasing concentrations of LEN (0 μM (control), 0.1 μM, 1 μM, and 10 μM) for 1 hour. The cells were then lysed, and the cell lysates were immunoprecipitated for EpoR, and immunoblotted for EpoR and RNF41. Increased binding of RNF41 to EpoR occurs in a concentration-dependent manner, suggesting that LEN promoted EpoR/RNF41 association in a concentration dependent manner.

Lenalidomide Inhibits the Autoubiquitination of RNF41 in a Concentration-dependent Fashion, and Inhibits Ubiquitation of EpoR To investigate the effects of LEN on RNF41 function, protein specific ubiquitination after proteasomal inhibition with bortezomib followed by LEN treatment was investigated. UT-7 cells were pre-treated with bortezomib (20 nM), a proteasome inhibitor, for 24 hours. The cells were subsequently treated with increasing concentrations of LEN (0 μM (control), 0.1 μM, 1 μM, and 10 μM) for 1 hour. The effect of LEN treatment on RNF41 was assessed through immunoprecipitation of RNF41 and immunoblotting for ubiquitin. To verify the observed effects, total protein levels in whole cell lysates were also assessed for RNF41 expression. In order to determine EpoR ubiquitination changes upon LEN treatment, immunoprecipitation of EpoR was carried out followed by immunoblotting for ubiquitin.

Immunoprecipitation of RNF41 and EpoR followed by ubiquitin immunoblotting suggested that LEN inhibited RNF41 auto-ubiquitination in a concentration-dependent fashion, accompanied by a corresponding decrease in EpoR ubiquitination. This suggested that LEN inhibits RNF41 ubiquitination to increase EpoR accumulation.

RNF41 Overexpression Abrogates LEN-induced EpoR Upregulation and Decreases Steady State EpoR Expression To confirm that RNF41 is the principal target of LEN responsible for EpoR stabilization, HEK293T cells were transfected with EpoR and/or RNF41 expression vectors using the calcium phosphate method. Transfected cells were treated with increasing concentrations of LEN (0 μM (control), 0.1 μM, 1 μM, and 10 μM) for 1 hour, separated by SDS-PAGE, and immunoblotted with EpoR antibodies. Steady state EpoR expression was lower in EpoR/RNF41 cells compared with cells transfected with EpoR alone.

The results of the densitometry analysis of EpoR and EpoR+pMet7-RNF41 HEK293T cells are shown in FIG. 1. Overexpression of RNF41 blocked LEN induced EpoR expression by approximately two-fold. This suggests that cellular RNF41 is a determinant of EpoR upregulation by LEN.

Immunohistochemical Analysis of Bone Marrow Biopsies from Non-del(5q) MDS Patients Treated with Lenalidomide 16 bone marrow biopsies were obtained from non-del(5q) LEN-treated MDS patients before and after treatment with LEN. RNF41 expression was assessed through dual-color immunohistochemical analysis. The samples were stained for RNF41 (brown) and spectrin (red), a known marker for erythroid progenitors.

Figure 2:
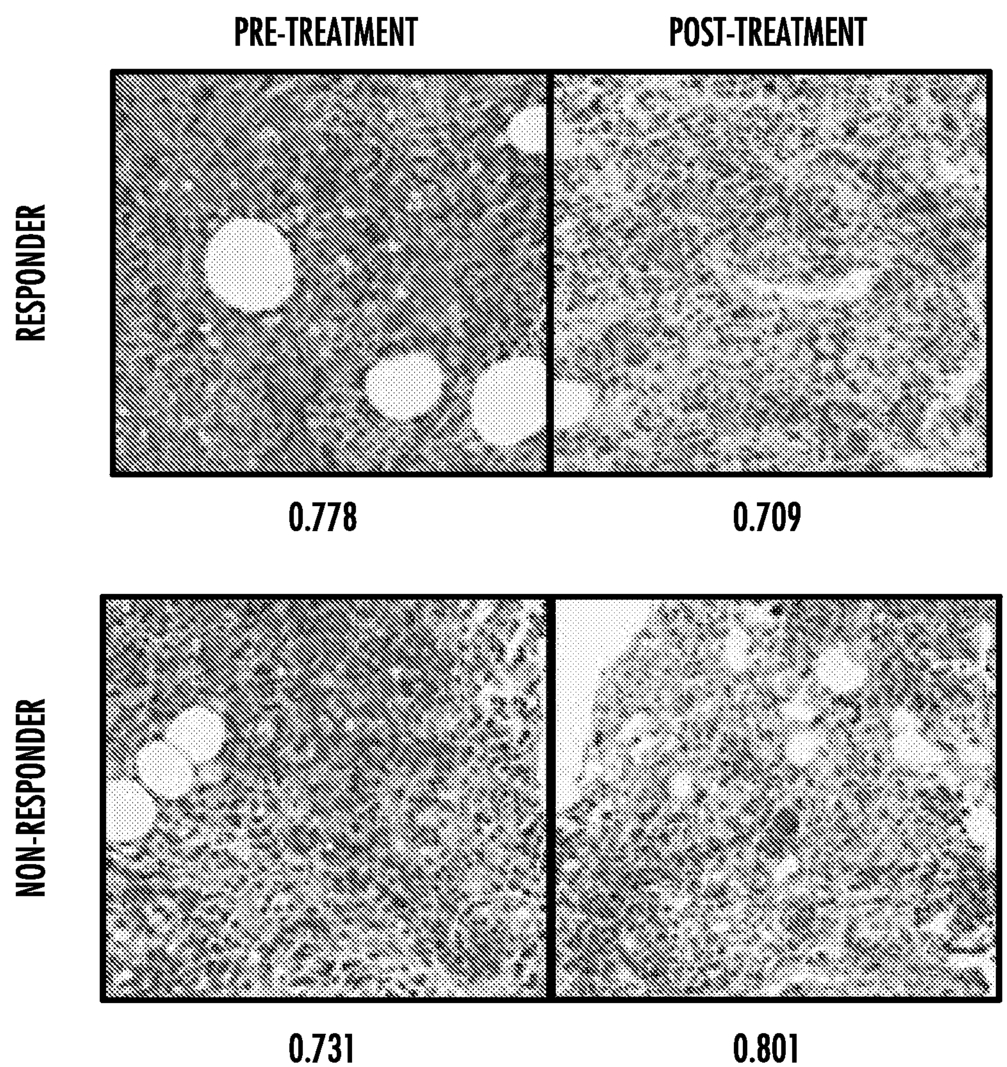
FIG. 2 shows the results of the dual-color immunohistochemical analysis of bone marrow biopsies from non-del (5q) MDS patients treated with lenalidomide.
Figure 3:
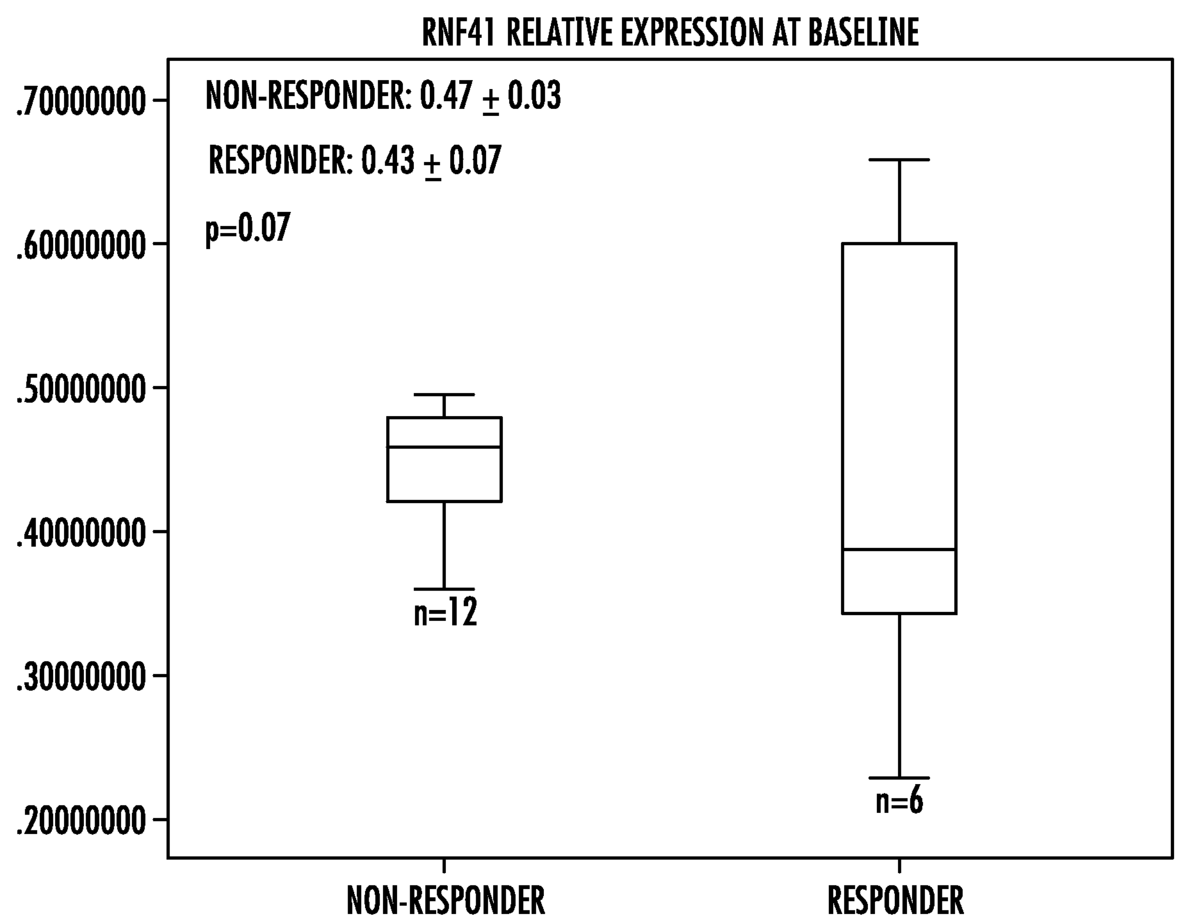
FIG. 3 is a plot of the relative expression of RNF41 at baseline in non-responders and responders from FIG. 2.

FIG. 2 shows pre and post-treatment images for a responder and a non-responder. The intensity of RNF41 in the erythroid stained cells in included below each image. As shown in FIG. 3, the relative expression of RNF41 at baseline is greater in non-responders than in responders, with the p-value approaching significance.

These findings demonstrate that LEN upregulates EpoR expression through inhibition of the E3-ubiquitin ligase RNF41. Overexpression of RNF41 inhibits LEN induced EpoR upregulation. Relative expression of RNF41 in erythroid precursors may therefore be used as a biomarker predictive for response to lenalidomide. Moreover, these studies indicate that the IMiDs have broad E3-ubiquitin ligase inhibitory effects.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject with non-del(5q) myelodysplastic syndrome (MDS), comprising a) measuring expression levels of Ring Finger Protein 41 (RNF41) in erythroid cells in a sample from the subject prior to treatment for MDS, and b) administering to the subject a therapeutically effective dose of lenalidomide (LEN), or a functional derivative thereof, if the levels of RNF41 are reduced compared to a control value established from one or more non-responders to LEN; or administering an alternative therapy for the subject if the levels of RNF41 are elevated compared to a control value established from one or more responders to LEN.

2. The method of claim 1, wherein the sample is a blood or bone marrow sample.

3. The method of claim 1, wherein RNF41 protein expression levels are measured using an immunoassay comprising an antibody that specifically binds RNF41.

4. The method of claim 3, wherein the immunoassay comprises enzyme-linked immunosorbent assay (ELISA), immunohistochemistry, or flow cytometery.

5. The method of claim 1, wherein RNF41 gene expression levels are measured using one or more oligonucleotides that function as primers or probes for detecting RNF41 gene expression levels.

6. The method of claim 1, comprising administering to the subject a therapeutically effective dose of LEN if mean levels of RNF41 in the subject sample are reduced by at least 10% compared to a value from a control sample from a known non-responder to LEN.

7. The method of claim 1, comprising treating the subject with 5-azacitidine or decitabine if mean levels of RNF41 in the subject sample are elevated by at least 10% compared to a value from a control sample from a known responder to LEN.

8. The method of claim 1, comprising treating the subject with 5-recombinant erythropoietins or antithymocyte globuli if mean levels of RNF41 in the subject sample are elevated by at least 10% compared to a value from a control sample from a known responder to LEN.

* * * * *